United States Patent
Hauser et al.

(10) Patent No.: US 9,291,561 B2
(45) Date of Patent: Mar. 22, 2016

(54) MOLECULAR NEAR-INFRARED TO VISIBLE LIGHT UPCONVERSION LUMINESCENCE

(75) Inventors: Andreas Hauser, Bern (CH); Claude Piguet, Plan-les-Quates (CH)

(73) Assignee: SICPA HOLDING SA, Prilly (CH)

( * ) Notice: Subject to any disclaimer, the term of this patent is extended or adjusted under 35 U.S.C. 154(b) by 294 days.

(21) Appl. No.: 13/980,231

(22) PCT Filed: Feb. 14, 2012

(86) PCT No.: PCT/IB2012/050667
§ 371 (c)(1),
(2), (4) Date: Jul. 17, 2013

(87) PCT Pub. No.: WO2012/110951
PCT Pub. Date: Aug. 23, 2012

(65) Prior Publication Data
US 2013/0299719 A1    Nov. 14, 2013

(30) Foreign Application Priority Data

Feb. 15, 2011    (EP) ..................................... 11154461

(51) Int. Cl.
*C07F 11/00*    (2006.01)
*B41M 3/14*    (2006.01)
*G01N 21/64*    (2006.01)

(52) U.S. Cl.
CPC ................ *G01N 21/64* (2013.01); *C07F 11/00* (2013.01)

(58) Field of Classification Search
USPC .................................... 546/2; 313/504; 427/7
See application file for complete search history.

(56) References Cited

PUBLICATIONS

Pope et al., Metal-to-ligand Charge-transfer Sensitisation of Near-infrared Emitting Lanthanides in Trimetallic Arrays M2Ln (M=Ru, Re or Os; Ln=nd, Er or Yb), Dalton Transactions, Apr. 21, 2005, pp. 1482-1490, XP002634032, No. 8, Cambridge, England.
Davies, Graham M. et al., Structural and Photophysical Properties of Coordination Networks Combining [Ru(bipy)(CN)4]2—Anions and Lanthanide(III) Cations: Rates of Photoinduced Ru-to-Lanthanide Energy Transfer and Sensitized Near-Infrared Luminescence, Inorganic Chemistry, Jun. 27, 2005, pp. 4656-4665, XP002634031, vol. 44, No. 13.
Cantuel, Martine et al., Encapsulation of Labile Trivalent Lanthanides into a Homobimetallic Chromium(III)-Containing Triple-Stranded Helicate. Synthesis, Characterization, and Divergent Intramolecular Energy Transfers, Dalton Transactions, Jun. 14, 2006, pp. 2647-2660, XP002634030, No. 22, Cambridge, England.
Chen, Fang-Fang et al., Sensitised Near-infrared Emission from Lanthanides Using an Iridium Complex as a Ligand in Heteronuclear Ir2Ln Arrays, Dalton Transactions, 2008, pp. 5577-5583, XP002634029.
Huang, Ping et al., Highly Efficient Near-infrared to Visible Upconversion Luminescence in Transparent Glass Ceramics Containing Yb3+/Er3+: NaYF4 Nanocrystals, Physica Status Solidi, pp. 1680-1684, XP002634028, vol. 205, No. 7.
Simpson, D.A., et al., Visible and Near Infra-red Up-conversion in Tm3+/Yb3+ co-doped Silica Fibers under 980 nm Excitation, Optics Express, Sep. 1, 2008, pp. 13781-13799, XP002634027, vol. 16, No. 18.
Reinhard, Christine et al., High-Resolution Optical Spectroscopy of Na3[Ln(dpa)3]·13H2O with Ln=Er3+, Tm3+, Yb3+, Inorganic Chemistry, Mar. 11, 2002, pp. 1048-1055, XP002634026, vol. 41, No. 5.
Balda, R., et al., Near Infrared to Visible Upconversion of Er3+ in CaZrO3/CaSZ Eutectic Crystals with Ordered Lamellar Microstructure, Journal of Luminenscence, Dec. 1, 2009, pp. 1422-1427, XP026697819, vol. 129, No. 12, Amsterdam, Netherlands.
Chinese Office Action issued with respect to application No. 201280008688.7, mail date is Feb. 15, 2015.
Lilit Aboshyan-Sorgho et al., "Near-Infrared—Visible Light Upconversion in a Molecular Trinuclear d-f-d Complex", Angew. Chem. Int. Ed. 2011, vol. 50, pp. 4108-4112.
Stephane Torelli et al., "Turning the decay time of Lanthanide-Based Near Infrared Luminescence from Micro-to Milliseconds through d-f Energy Transfer in Discrete Heterobimetallic Complexes", Chem. Eur. J., 2005, 11, pp. 3228-3242.

*Primary Examiner* — Charanjit Aulakh
(74) *Attorney, Agent, or Firm* — Greenblum & Bernstein, P.L.C.

(57) ABSTRACT

The present invention relates to a self-assembled helical metallic complex of formula (1): $[M_1M_2M_3(L1)_3]$ (1) said metallic complex forming a triad donor $(M_1)$/acceptor $(M_2)$/donor $(M_3)$, wherein the efficiency of the intermolecular energy transfer between the pair of donors (M\) and (M3) to the acceptor $(M_2)$ is from 30% to 70% and the L1 ligand-field strength of the donors $(M_1)$ and $(M_3)$ is at least 19000 $cm^{-1}$.

19 Claims, 2 Drawing Sheets

MOLECULAR NEAR-INFRARED TO VISIBLE LIGHT UPCONVERSION LUMINESCENCE

TECHNICAL FIELD

The present invention relates to the field of metallic complexes, in particular self-assembled helical metallic complexes for performing molecular upconversion luminescence from infrared or near-infrared light to visible light. More particularly, the present invention relates to metallic complexes for use in bio-imaging as detection means and/or as a target means in photodynamic therapy and/or upconverter in dye-sensitized solar cells and/or for use in the protection of value documents and/or value commercial goods against counterfeiting and illegal reproduction.

PRIOR ART AND THE PROBLEM UNDERLYING THE INVENTION

Upconversion has been regularly reported for trivalent lanthanide cations doped into low-phonon inorganic matrices, particularly for applications in bio-analyses, telecommunications, and solar energy conversion, but it is still unknown in molecular erbium complexes because of the high effective vibrational energy typical of the molecular vibrations of organic ligands or of closely interacting solvent molecules, which result in efficient non-radiative relaxation of 4f-4f transitions.

Beyond the optimization of polarizable push-pull π-aromatic molecules for NLO optical response, and the related development of upconverted fluorescence signals in polyaromatic platforms produced by metal-sensitized triplet-triplet annihilation photochemistry, Tancrez et al. demonstrated that trivalent lanthanides may efficiently contribute to the polarization of coordinated aromatic ligands for resonant multiphoton absorption (Tancrez, N.; Feuvrie, C.; Ledoux, I.; Zyss, J.; Toupet, L.; Le Bozec, H.; Maury, O. J. Am. Chem. Soc. 2005, 127, 13474-13475). The latter phenomenon corresponds to a purely non-linear optical process, which does not involve intermediate electronic relays as those found in the upconversion mechanism implemented in the Cr/Er/Cr triad of the invention described further below.

Molecular non-linear optical (NLO) phenomena are currently exploited for the design of visible emitting bioprobes for bio-imaging with unprecedented properties resulting from (i) the transparency of living tissues toward low-energy near-infrared incident radiations and (ii) the improved focusing of the light from the excitation laser beam within nanometric volumes. Moreover, the wealth of accessible long-lived metal-centered luminescent emissive levels can be exploited for two-photon excited time-gated fluorescent analyses of biological tissues.

Moreover, most luminescent probes used for bio-imaging today, such as organic fluorophores or luminescent semiconducting nanocristals (so called "quantum dots") operate in a light spectrum where biological matter self-fluoresces. The signal/noise ratio is consequently poor, making observation more difficult. Other probes available in the market emit in the infrared (IR) requiring expensive IR cameras for observation.

In the technology of the photoelectrochemical or optoelectronic device, such photoelectric conversion devices in particular dye-sensitized solar cell, photovoltaic cell are capable of converting electromagnetic radiation, in particular visible, infrared and/or UV light, in particular sunlight, into electrical current. However a part of the light spectrum, in particular infrared light, is not trapped by the present dyes or sensitizers. Therefore, the efficiency of such a device is decreased.

In the field of the protection of value documents and value commercial goods against counterfeiting, falsifying and illegal reproduction, security elements are highly required. In particular, luminescent compounds are widely used as marking materials in security applications. For example, luminescent compounds are suitable for the realization of machine-readable security elements.

In the state of the art, several publications report the upconversion of trivalent 4f-block activators (erbium, thullium, ytterbium, neodymium, praseodymium, e.g.) co-doped with d- or f-block sensitizers block in low-phonon ionic solids or nanoparticles (Balda et al., Jlumin., 2009, 129, 1422-1427; Simpson et al., Optic Express, 2008, 16, 18, 13781-13799; Huang et al., Phys. Stat. sol., 2008, (a) 205, 7, 1680-1684). All these infinite solids, which are not metallic complexes but metallic cations doped in ionic solids, do not behave as discrete molecules, in particular in solution or in gelified solution. On the contrary of a molecule existing as an infinite molecular solid, the infinite ionic solids or nanoparticles are separated into their components. Accordingly, they lose their structure and properties. Said molecules, when dispersed in a solvent, remain intact.

Furthermore, in the field of the search for upconversion fluorescence in the molecular complexes $Na_3[Ln(pyridine-2,6-dicarboxylate)_3] \cdot 13 H_2O$ (Ln=Nd, Er, Yb), Reinhard and Güdel indeed concluded that 'There is no chance to induce and observe upconversion luminescence in these molecular compounds' (Inorg. Chem. 2002, 41, 1048-1055).

From the state of the art, it is known that metallic complexes may comprise polycyclic molecule, in particular polypyridine as ligand to form heteronuclear d-f complexes with lanthanide metal through lanthanide-bridged complexes, which emit in the near infra-red (NIR) (Chen et al., Dalton Trans., 2008, 5577-5583; Davies et al., 2005, Inorg. Chem. 44, 4656-4665; Pope et al., Dalton Trans., 2005, 1482-1490). However none of these complexes are helical complexes, which comprise polycyclic ligand strands bound to the metals and which assume a helical conformation of the complexes. Moreover none of them absorbs in the NIR.

Reconsidering some fundamental rate equations as further described in the example of the invention, the inventors found that a metallic complex of the invention is indeed able to address the problems depicted above.

In particular, the present invention addresses the objectives of providing new metallic molecular complexes, which are reproductive complexes on the contrary of solid complexes, self-assembled for the upconversion fluorescence of near and infrared light into visible light in solution or gelified solution, resulting in detection means for the bio-imaging and/or in target means for photodynamic therapy, and/or in improving the absorption spectrum of photoelectrochemical and/or optoelectronic devices and the energy conversion efficiency.

With the metallic complex according to the invention, it is possible to have bio-imaging probes (detection means) which emit in the visible while being activated with IR, a part of the spectrum, which does not interact with biological matter. Therefore, the self-fluorescence is avoided. Another advantage of the use of such a metallic complex in the bio-imaging technology is that standard optical microscopes instead of expensive IR cameras can be used. Moreover, IR light is a non-ionizing radiation, what also represents an advantage compared to other techniques of bio-imaging. Also, being a molecular compound, it can be better controlled than nanoparticles in terms of synthesis, composition, analysis, measurements, conformation, distribution, binding to other molecules or compounds etc.

The metallic complexes according to the invention provide small luminescent molecules allowing dye-sensitized photovoltaic cells to benefit from the untrapped IR part of the sun radiation by "upconverting" it to the visible range. This way, the IR spectrum of the sun offers additional displacement and separation of charges in dye-sensitized photovoltaic cells, increasing the yield of such systems significantly. Up to now, this has been the main limitation of this technology.

The metallic complexes according to the invention provide luminescent molecules as security element for protecting value documents and value commercial goods and/or preventing counterfeiting or illegal reproduction of said value documents or said value commercial goods.

SUMMARY OF INVENTION

In an aspect, the present invention provides a helical metallic complex comprising at least three metal atoms, two of said metal atoms ($M_1$, $M_3$) being selected in the group consisting of metal d and metal f, metal $M_1$ and $M_3$ being the same metal, and at least one metal atom ($M_2$) being selected from metal f, wherein said complex comprises at least three polycyclic ligand molecules comprising heteroatoms, preferably amine groups, so as to form a complex with said metal atoms, wherein each of said polycyclic molecules is bound to at least two, preferably three, metal atoms, wherein said polycyclic molecules assumes a helical conformation and said metals are bound in the centre of said helical conformation, and wherein said metal $M_2$ is situated in between metals $M_1$ and $M_3$. In case more than three metals are present, the next metal ($M_4$) is preferably the same as $M_2$, $M_5$, if applicable, is the same as $M_1$ and $M_3$, and so forth.

In an aspect, the present invention provides a self-assembled helical metallic complex of formula (1):

$$[M_1M_2M_3(L1)_3] \quad (1)$$

wherein:
$M_1$ and $M_3$ are metal elements selected in the group consisting of metal d and metal f, with the proviso that $M_1$ and $M_3$ are of same metal elements,
$M_2$ is a metal selected in the group consisting of metal f,
L1 is a ligand being a polycyclic chemical molecule,
wherein said complex is neutral or charged
each $M_1$, $M_2$, and $M_3$ is surrounded by three L1,
and said metallic complex forming a triad donor ($M_1$)/acceptor ($M_2$)/donor ($M_3$), wherein the efficiency of the intermolecular energy transfer between the pair of donors ($M_1$) and ($M_3$) to the acceptor ($M_2$) is from 30% to 70% and the L1 ligand-field strength of the donors ($M_1$) and ($M_3$) is at least 19000 $cm^{-1}$.

In another aspect, the present invention provides photo-electrochemical and/or optoelectronic devices comprising such a metallic complex according to the invention.

In further aspects, the present invention relates to the use of a metallic complex according to the invention in bio-imaging as a detection means and the use of such metallic complex in photodynamic therapy as a target means.

In an aspect, the present invention provides a method of upconversion of light comprising:
providing a metallic complex according to the invention;
irradiating said metallic complex with infrared light from light source;
detecting emitted light in the visible spectrum by said irradiated metallic complex.

In a further aspect, the invention provides a method of upconversion of light comprising the steps of providing a metallic complex according to the complex of the invention, exposing said metallic complex to a light source comprising infrared light; and thereby upconverting said infrared light, in particular to light of the visible spectrum.

In a further aspect, the invention provides the use of a metallic complex of the invention as a security element for value documents and/or value commercial goods to prevent counterfeiting, security element comprising said metallic complex and value documents or value commercial good comprising said security element.

Further aspects and preferred embodiments of the present invention are detailed in the appended claims and the detailed description below.

DETAILED DESCRIPTION OF THE PREFERRED EMBODIMENTS

Figure 1:
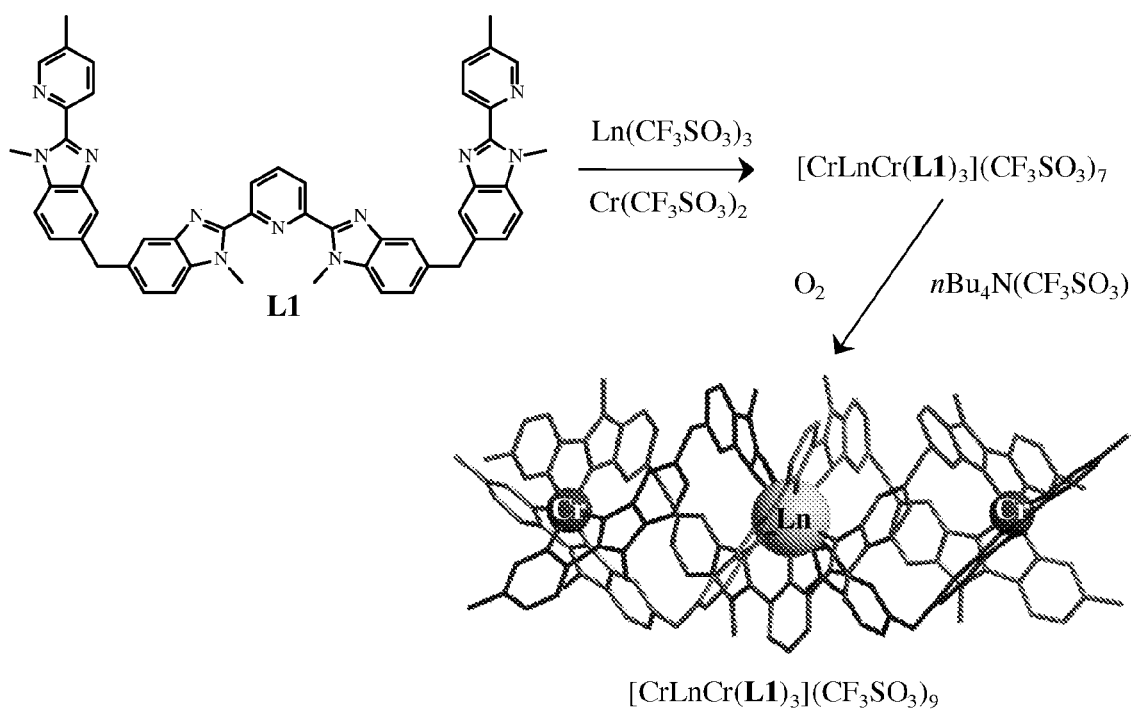
FIG. 1 shows the synthesis of the kinetically inert dimetallic d-f-d complexes of formula (1) [CrLnCr(L1)$_3$](CF$_3$SO$_3$)$_9$.

The present invention relates to self-assembled helical metallic complex performing the upconversion of near- and/or infrared light to visible light. Said metallic complex represents a triad donor/acceptor/donor or sensitizer/acceptor/sensitizer. An attractive sensitizer/acceptor pair for potential molecular upconversion should thus match the following three criteria: 1) each acceptor should be surrounded by at least two equidistant sensitizers, 2) the resonant S→A (sensitizer→acceptor) energy transfer processes is optimized for an efficient population of the excited levels of the acceptor, while ensuring a long enough excited state lifetimes of the remaining sensitizers for the occurrence of sequential energy transfer in an isolated molecule, 3) the acceptor must be protected from high-frequency vibrations in order to minimize the average energy of the interacting phonons. These parameters are further described and determined in the example of the invention.

Accordingly, in one embodiment, the at least three metal atoms ($M_1$, $M_2$ and $M_3$) in said metallic complex are sequentially arranged and embedded within a triple helix formed by said at least three polycyclic ligand molecules represented by L1.

According to one embodiment, the metal of each donor or sensitizer $M_1$, $M_3$ of the triad belongs either to metal d, which is selected from Sc, Ti, V, Cr, Mn, Fe, Co, Ni, Y, Zr, Nb, Mo, Tc, Ru, Rh, Pd, Lu, Hf, Ta, W, Re, Os, Ir, Pt, or to metal f, which is selected from La, Ce, Pr, Nd, Pm, Sm Eu, Gd, Tb, Dy, Ho, Er, Tm, Yb. Preferably, $Cr^{III}$ is metal d of choice for the two sensitizers or donors of the triad.

In a further embodiment, the metal of the acceptor $M_2$ of the triad belongs to metal f, which is selected from La, Ce, Pr, Nd, Pm, Sm Eu, Gd, Tb, Dy, Ho, Er, Tm, Yb. Preferably, metal f is selected from Tm, Er, Yb, and more preferably metal f is $Er^{III}$.

According to an embodiment, metals of the triad or said metallic complexes are preferably $Cr^{III}$/Ln/$Cr^{III}$ with Ln selected in the group of Tm, Er, Yb. More preferably, metals of the triad or said metallic complex are $Cr^{III}$/$Er^{III}$/$Cr^{III}$, namely two $Cr^{III}$ for the sensitizers or the donors and $Er^{III}$ for the acceptor. Without binding by the theory, $Cr^{III}$ sensitizers are therefore in strong ligand-field environments in order to push the $Cr(^4T_2)$ excited states, and the associated broad absorption band, to sufficiently high energy, while the comparatively large nephelauxetic effect lowers the energy of the $^2E$ state of $Cr^{III}$ around 13400 $cm^{-1}$.

The metallic complex of formula (1) may be charged or neutral depending on the ligand and on its environment.

In another embodiment, L1 comprises polycyclic groups or a chain or sequence of cyclic groups selected, independently one from the other, from the group of pyridine, polypyridine, azole, polyazole, pyrazole, imidazole, benzimidazole, and wherein the terminal cyclic groups of said chemical molecule comprise at least one amine group. Preferably, L1 is a ligand of formula (2)

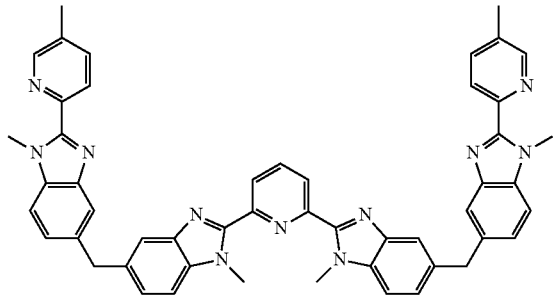

(2)

Without binding by the theory, three molecules of L1 form triple helical structure around $M_1$, $M_2$ and $M_3$, wherein said structure is self-assembled. (FIG. 1)

According to the invention, the efficiency of the intermolecular energy transfer between the donors $M_1$ and $M_3$ to the acceptor $M_2$ is from 30% to 70%, and preferably is 50% and the L1 ligand-field strength of the donors $M_1$ and $M_3$ is at least 19000 $cm^{-1}$, preferably between 19000 $cm^{-1}$ and 24000 $cm^{-1}$, more preferably 20980 $cm^{-1}$.

In a further embodiment, the metallic complex absorbs light in the spectrum of infrared and emits light in the visible spectrum.

According to one embodiment, the metallic complex according to the invention is soluble in solution and/or gelified solution. Gelified solution may be nanoparticles, organic or bio-polymer, gel, biological matrix, or membrane.

According to another embodiment, detection means may be selected in the group comprising probes, vectors, DNA probes, RNA probes, peptide, protein or antibody, wherein a metallic complex according to the invention is directly bound or linked through a linker. The detection means is also similar to a biosensor to analyse the presence of a target, which may be DNA, RNA, peptide, bacteriae, virus, protein, analytes or to detect the flux of biological fluid.

According to another embodiment, the metallic complex of the invention, in particular $CrErCr(L1)_3$, may be used as a security feature material in a security element for the protection against counterfeiting of a security document, a value document or a value commercial good including without limitation banknotes, value documents or cards, transportation tickets or cards, tax banderols, and product labels. Advantageously, the metallic complex of the invention, in particular $CrErCr(L1)_3$, may be used as a machine readable security feature material. Typically, the metallic complex of the invention, in particular $CrErCr(L1)_3$, may be incorporated as a security feature material into an ink or coating composition so as to be applied onto the security document. The metallic complex of the invention, in particular $CrErCr(L1)_3$ may be dissolved or dispersed within a polymer binder component of the ink or coating composition. Alternatively, the metallic complex of the invention, in particular $CrErCr(L1)_3$, may be incorporated as a security feature material in the security document; in particular it may be incorporated in the substrate of the security document, the substrate including without limitation fibrous materials (e.g. celluloses and paper-containing materials), plastics, polymers, composite materials, metals or metalized materials and combinations thereof.

EXAMPLE

Preparation of $[CrErCr(L1)_3](CF_3SO_3)_9 (H_2O)_{17}$.

A solution of $Er(CF_3SO_3)_3 \cdot 3 H_2O$ in acetonitrile was added to a solution of L1 in acetonitrile/dichloromethane. After stiffing for 12 h. at RT, the solvent was removed under vacuum and the residue transferred into a glove box under an inert atmosphere. Dissolution into degassed acetonitrile, followed by the addition of a deep blue solution of $Cr(CF_3SO_3)_2 \cdot H_2O$ in acetonitrile produced a deep green mixture, which was stirred for one night under an inert atmosphere. $nBu_4N(CF_3SO_3)$ was added, followed by slow bubbling of air for two hours. The solution turned orange, the solvent was removed, and the solid residue dissolved in acetonitrile. Crystallization by using slow diffusion of diethylether provided 68 mg of orange microcrystalline powders of $[CrErCr(L1)_3](CF_3SO_3)_9 \cdot (H_2O)_{17}$. Elemental analysis calcd (%) for $C_{162}H_{163}Cr_2ErF_{27}N_{33}O_{44}S_9$: C, 44.74, H, 3.78, N, 10.62; found. C, 44.70, H, 3.56, N, 10.48. Suitable Xray quality needles of $[CrLnCr(L1)_3]_2(CF_3SO_3)_{18}(C_3H_5N)_{30}$ (Ln=Eu: 1 and Ln=Yb: 2) were obtained by slow diffusion of diethylether into concentrated proprionitrile solutions of the aqueous complexes.

Spectroscopic and Analytical Measurements.

Pneumatically-assisted electrospray (ESI-MS) mass spectra were recorded from $10^{-4}$ M solutions on a Finnigan SSQ700 instrument. Electronic S3 spectra in the UV-Vis were recorded at 293 K from solutions in MeCN with a Perkin-Elmer Lambda 900 spectrometer using quartz cells of 0.1 path length.

Powder samples were mounted directly onto copper plates using either rubber cement or conductive silver glue and cooled either in an optical closed-cycle cryostat capable of reaching low temperatures up to 10 K in an helium atmosphere (CTI-Cryogenics, Oxford Instruments, CCC1100T) or with a liquid-helium bath cryostat (Sumitomo SHI-4-5 or Oxford Instruments MD4). For room temperature or 77K measurements, the samples were transferred into quartz tubes or borosilicate glass tubes and were closed with Parafilm. Room temperature and 77 K emission and excitation spectra were measured on a LS-50B Fluorescence Spectrometer (Perkin Elmer) or Fluorolog-3 spectrometer (Jobin Yvon Horiba FL3-22) equipped with different detectors, i.e. a thermo-electrically cooled (−60° C.) photomultiplier (Hamamatsu H9170-75 sensitivity: 950-1700 nm) to measure the Er3+(4I13/2 à 4I15/2) transition lying between 1450 and 1650 nm. High resolution room temperature and low temperature (3.5 K) emission spectra were performed upon excitation with an Ar+ laser (Coherent Innova 90C) at 488 nm or with Nd:YAG laser (Newport Millenia-1OSJ) at 355 nm. The emitted light was analyzed at 90° with a Spex 270M monochromator blazed at 600 nm with holographic gratings (150l/ mm). Light intensity was measured by a photomultipliers or CCD detectors. Appropriate filters were utilized to remove the laser light, the Rayleigh scattered light and associated harmonics from the emission spectra. The emission spectra were corrected for the instrumental function. Luminescent lifetimes were measured using excitation provided by a Quantum Brillant Nd:YAG laser equipped with frequency doubler, tripler and quadrupler as well as with an OPOTEK MagicPrism™ OPO crystal. The output signal of the photomultiplier was fed into a Stanford Research SR-400 multichannel scaler and transferred to a PC. Lifetimes are averages of 3 independent determinations. Resonant excitation into the $^4A_2 \rightarrow ^2E$ transition of $Cr^{3+}$ in CrErCr was achieved with a tunable Ti:sapphire laser (Spectra Physics 3900S) pumped by the S4 532 nm excitation of a Nd:YAG laser (Newport Millenia-1OSJ). The excitation was tuned to 13360-13890 cm$^{-1}$. A short pass filter that cuts the scattered laser light and allows the passing of green light was used for these measurements. Any pump laser was removed at the exit of the Ti:sapphire laser with an RG 715 nm color filter. The excitation spectra were corrected for the emission of the Xenon lamp, and the emission spectra were corrected for the instrumental response (wavelength dependence of the dispersion of the monochromator and the detector sensitivity). The spectra were displayed as photons versus energy (cm$^{-1}$).

Following Auzel's kinetic approach, the probabilities for the two-photon excitation processes $W_{G \rightarrow E}$ are simply given by equations 1 and 2, respectively, where $W_{SA}$ are the Sensitizer→Acceptor energy transfer probabilities for each step and $N^*_S = N_S W_{G \rightarrow E(1)}$ is the concentration of the excited sensitizers acting as donors for the acceptor.

$$W_{G \rightarrow E(2)}^{ESA} = W_{G \rightarrow E(1)} \cdot W_{E(1) \rightarrow E(2)} \quad (1)$$

$$W_{G \rightarrow E(2)}^{ETU} = (N_S^* \cdot W_{SA1}) \cdot (N_S^* \cdot W_{SA2}) = (N_S)^2 \cdot W_{SA1} \cdot W_{SA2} \cdot (W_{G \rightarrow E(1)})^2 \quad (2)$$

Assuming that $W_{G \rightarrow E(1)} \sim W_{E(1) \rightarrow E(2)}$, a well-accepted approximation for rare earth ions, comparison of eqs 1 and 2 shows that the Energy Transfer Upconversion (ETU) process may benefit from chemical tuning via (i) a large local concentration of sensitizers, thus maximizing $N_S$ around each acceptor and (ii) efficient resonant S→A energy transfer processes maximizing $W_{SA1}$ and $W_{SA2}$.

Based on previous studies, a $Cr^{III}/Er^{III}/CR^{III}$ triad appears to be a good candidate with the two $Cr^{III}$ sensitizers in strong ligand-field environments in order to push the $Cr(^4T_2)$ excited states, and the associated broad absorption bands, to sufficiently high energy, while the comparatively large nephelauxetic effect lowers the energy of the $^2E$ state of $Cr^{III}$ around 13400 cm$^{-1}$. These conditions are required for the fine tuning of the target intermetallic $Cr(^2E) \rightarrow Er(^4I_{9/2})$ energy transfer. With this in mind, we reacted the segmental ligand L1 with stoichiometric amounts of $Ln(CF_3SO_3)_3 \cdot x H_2O$ (Ln=Eu, Gd, Er, Yb) and $Cr(CF_3SO_3)_2 \cdot H_2O$ in acetonitrile to give the self-assembled helical pseudo-cryptates $[CrLnCr(L1)_3]^{7+}$, which were eventually oxidized into the kinetically inert triple-helical complexes $[CrLnCr(L1)3]^{9+}$ (FIG. 1).

Fine crystalline orange needles suitable for X-ray diffraction studies could be isolated from slow diffusion of diethyl ether into concentrated propionitrile solutions of $[CrLnCr(L1)_3](CF_3SO_3)_9$ (Ln=Eu, Yb). According to the minute dimensions of the crystals combined with the huge cell parameters, X-ray radiation from a synchrotron was used for solving the crystal structure of $[CrEuCr(L1)_3]_2(CF_3SO_3)_{18}(C_3H_5N)_{30}$ ($P2_1/c$), while a standard setup was used for confirming isostructurality with Ln=Yb. All Cr—N and Ln—N bond lengths are standard, and the global pseudo-D3 symmetrical triple-helical cation $[CrLnCr(L1)_3]^{9+}$ is made up of a pseudo-tricapped trigonal LnN9 prism sandwiched between two pseudo-octahedral $CrN_6$ moieties (FIG. 1). Two slightly different cations with opposite helicities exist in the asymmetric unit, but the geometrical differences, except for the chirality, are marginal. We conclude that the three metals in $[CrLnCr(L1)_3]^{9+}$ are (i) aligned along a pseudo-threefold axis, (ii) protected from the solvent by the wrapping of the three helical ligand strands and (iii) regularly spaced with Cr . . . Eu=8.8(1) Å and Cr . . . Yb=8.9(1) Å. Based on the Jablonski diagram previously established for $[CrGdCr(L1)_3]^{9+}$ (termed CrGdCr), UV irradiation of the complexes $[CrErCr(L1)_3]^{9+}$ (CrErCr) efficiently populates ligand-centered $\pi\pi^*$ excited states. Subsequent partial L1→$Cr^{III}$ and L1→$Er^{III}$ energy transfer processes followed by internal relaxation processes eventually yield rich mixed ligand-centered and metal-centered luminescence as previously described for several $Cr^{III}/Ln^{III}$ pairs in molecular complexes. From the excitation spectrum of CrErCr recorded upon monitoring the red $Cr(^2E \rightarrow ^4A_2)$ emission band at 13380 cm$^{-1}$, we can easily locate the low-energy spin-allowed $Cr(^4T_2 \rightarrow ^4A_2)$ transition at around 20980 cm$^{-1}$, a band which is further split by pseudo-D$_3$ symmetry into A+E components. Since the energy of the latter transition exactly matches the ligand field-strength for d3 metals in octahedral geometry, we deduce that 10Dq(Cr)~20980 cm-1 in CrErCr, a value which compares well with the 23240 cm-1 found for $[Cr(bpy)_3]^{3+}$, in which bpy is the strong-field didentate 2,2'-bipyridine ligand.

Accordingly, the coordination spheres around $Cr^{III}$ in the trinuclear complexes CrLnCr indeed discriminates the energies of the $Cr(^4T_2)$ and $Cr(^2E)$ levels to such an extent ($\Delta E = 20980 - 13380 = 7600$ cm$^{-1}$) that only the latter excited state can act as a feeding level for energy transfer towards $Er^{III}$, while $Cr(^4T_2)$ is inefficient. This situation is ideal for a quantitative analysis of the intermetallic energy transfer process. Upon selective irradiation of the $Cr(^4T_2 \leftarrow ^4A_2)$ transition in CrErCr at 22220 cm$^{-1}$, internal relaxation via intersystem crossing rapidly feeds the $Cr(^2E)$ excited states, which simultaneously luminesce in the red ($Cr(^2E \rightarrow ^4A_2)$, $\tilde{v}_{em} = 13380$ cm$^{-1}$, full width at half height fwhh=420 cm$^{-1}$) and transfer energy onto $Er^{III}$ ($Cr(^2E) \rightarrow Er(^4I_{912})$). Basic rate equations written for the time evolution of the population of the $Cr(^2E)$ excited states in CrGdCr (eq 3, $k_{rad}$ and $k_{nr}$ are respectively the intrinsic radiative and non-radiative relaxation rate constants) and in CrErCr (equation 4, $k_{EnT}^{Cr,Er}$ is the rate constant for Cr→Er energy transfer) allow the estimation of the rate (equation 5, $k_{EnT}^{Cr,Er} = 4.9(2) \cdot 10^2$ s$^{-1}$) and efficiency (equation 6, $\eta_{EnT}^{Cr,Er} = 53\%$) of the intramolecular $Cr(^2E) \rightarrow Er(^4I_{9/2})$ energy transfer by simply using the characteristic $Cr(^2E)$ lifetimes experimentally measured for CrGdCr ($\tau_{obs}^{Cr}$(CrGdCr)=2.27 ms at 10 K) and for CrErCr ($\tau_{obs}^{Cr}$(CrErCr)=1.07 ms at 10 K).

$$k_{obs}^{Cr}(CrGdCr) = k_{rad}^{Cr} + k_{nr}^{Cr} = 1/\tau_{obs}^{Cr}(CrGdCr) \quad (3)$$

$$k_{obs}^{Cr}(CrErCr) = k_{rad}^{Cr} + k_{nr}^{Cr} = 1/\tau_{obs}^{Cr}(CrErCr) \quad (4)$$

$$\begin{aligned} k_{EnT}^{Cr,Er} &= k_{obs}^{Cr}(CrErCr) - k_{obs}^{Cr}(CrGdCr) \\ &= 1/\tau_{obs}^{Cr}(CrErCr) - 1/\tau_{obs}^{Cr}(CrGrCr) \end{aligned} \quad (5)$$

-continued $$\eta_{EnT}^{Cr,Er} = \frac{k_{EnT}^{Cr,Er}}{k_{rad}^{Cr} + k_{nr}^{Cr} + k_{EnT}^{Cr,Er}} \quad (6)$$

$$= \frac{k_{obs}^{Cr}(CrErCr) - k_{obs}^{Cr}(CrGdCr)}{k_{obs}^{Cr}(CrErCr)}$$

$$= 1 - \frac{\tau_{obs}^{Cr}(CrErCr)}{\tau_{obs}^{Cr}(CrGdCr)}$$

We are finally equipped for exploring the sequential energy transfer upconversion (ETU) phenomenon in the molecular CrErCr complex, in which the central $Er^{III}$ acceptor is sandwiched between two strong-field $Cr^{III}$ sensitizers possessing $Cr(^2E)$ levels adapted for feeding the $Er(^4I_{9/2})$ level (i.e. about 50% efficiency at 10 K with millisecond residual lifetimes). Though very weak because of the spin selection rules, the excitation spectra of CrErCr indicates that direct excitation of the $Cr(^2T_1, ^2E \leftarrow ^4A_2)$ transitions with near-infrared light is conceivable (13200-13800 $cm^{-1}$). Consequently, irradiation at 13333 $cm^{-1}$ with a tunable Ti-sapphire laser with power in the range 195-690 mW/mm$^2$ indeed produces upconversion luminescence with the detection of the wellknown $Er(^4S_{3/2} \rightarrow ^4I_{15/2})$ green emission at 18400 $cm^{-1}$ (FIG. 2).

Figure 2:
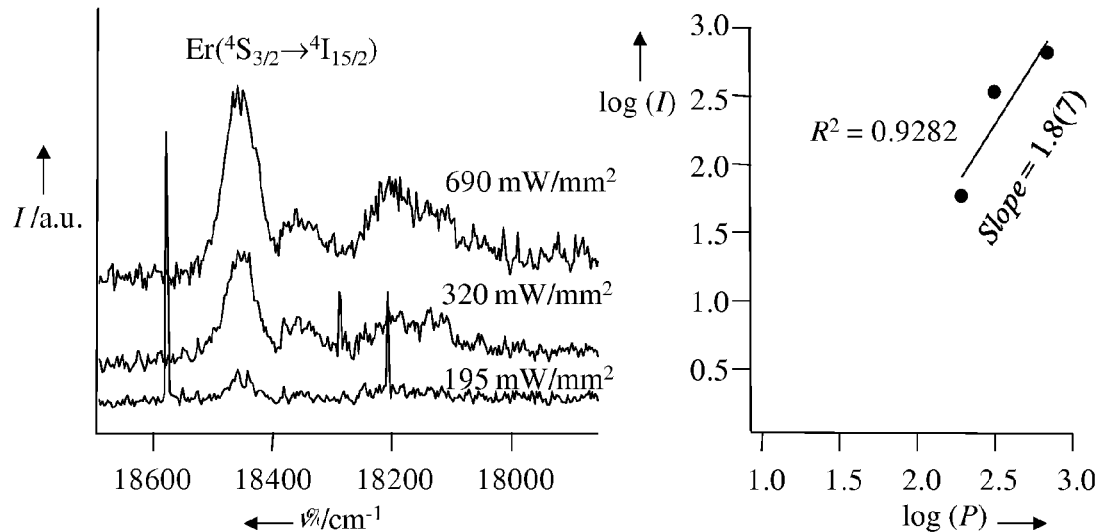
FIG. 2 shows non-linear green upconversion luminescence in [CrErCr(L1)$_3$](CF$_3$SO$_3$)$_9$ obtained upon irradiation of the Cr($^2$E←$^4$A$_2$) transition at varying laser powers: in solid state (4 K, $v_{exc}$=13333 $cm^{-1}$)
Figure 3:
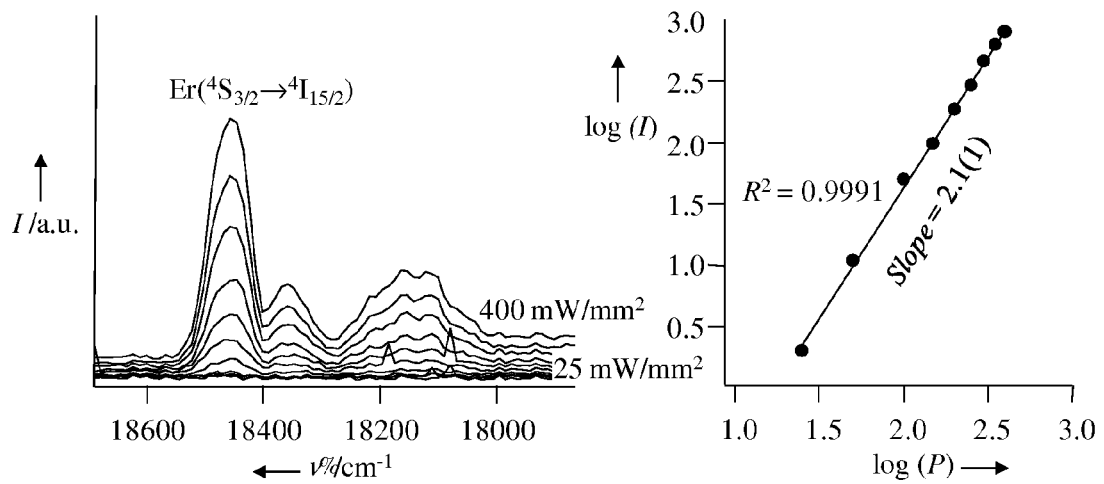
FIG. 3 shows non-linear green upconversion luminescence in [CrErCr(L1)$_3$](CF$_3$SO$_3$)$_9$ obtained upon irradiation of the Cr($^2$E←$^4$A$_2$) transition at varying laser powers: in 10 mM in acetonitrile ($v_{exc}$=13360 $cm^{-1}$, 30.6 K).

From FIG. 2 and FIG. 3, we therefore conclude that the connection of two chromium(III) sensitizers around a central erbium(III) acceptor in a self-assembled cationic complex provides high local concentrations favoring efficient nonlinear Energy Transfer Upconversion (ETU) luminescence. Upon selective low-energy near-infrared irradiation of Cr centered transitions, $[CrErCr(L1)_3]^{9+}$ displays an unprecedented molecular two-photon upconverted green Er-centered emission.

To the best of our knowledge, $[CrErCr(L1)_3]^{9+}$ is the first report of an isolated molecular system displaying Near InfraRed→Visible upconversion, a rare phenomenon induced by the specific molecular and electronic design, which strongly favours nonlinear sequential energy transfer upconversion. The high concentration of sensitizers combined with (i) the tuned 50% efficiency of the intramolecular Cr→Er energy transfer, (ii) the long residual lifetime of the sensitizer excited states and (iii) the protection of $Er^{III}$ from high-energy oscillators contribute to the detection of measurable molecular upconversion in a diluted medium. It is worth noting the operation of a strict two-photon upconversion process when two chromium ions sandwich erbium in CrErCr. Since $Er^{III}$ possesses several closely spaced excited states covering the infrared to ultra-violet range, we tentatively infer that the connection of three strong-field $Cr^{III}$ around this specific trivalent lanthanide may lead to unprecedented three-photon upconversion luminescence.

The invention claimed is:

1. A security element comprising a helical metallic complex as a security feature material, the helical metallic complex comprising at least three metal atoms, $M_1$, $M_2$ and $M_3$, two of said metal atoms $M_1$ and $M_3$ are selected from Sc, Ti, V, Cr, Mn, Fe, Co, Ni, Y, Zr, Nb, Mo, Tc, Ru, Rh, Pd, Lu, Hf, Ta, W, Re, Os, Ir, Pt, La, Ce, Pr, Nd, Pm, Sm Eu, Gd, Tb, Dy, Ho, Er, Tm, Yb, metal $M_1$ and $M_3$ being the same metal atoms, and at least one metal atom $M_2$ being selected from Tm, Er, Yb, wherein said complex comprises at least two benzimidazole molecules, so as to form a complex with said metal atoms, wherein each of said benzimidazole molecules is bound to at least two metal atoms, wherein said benzimidazole molecules assume a helical conformation and said metals are bound in the center of the helical conformation, wherein the metal $M_2$ is situated between metals $M_1$ and $M_3$; and the metallic complex absorbs light in the spectrum of infrared and emits light in the visible spectrum.

2. The security element according to claim 1, wherein the security element comprises an ink.

3. The security element according to claim 1, wherein the security element comprises a coating.

4. The security element according to claim 1, wherein the security element comprises a security document, a value document or a value commercial good.

5. The security element according to claim 1, wherein the security element comprises a banknote, a value document or card, a transportation ticket or card, a tax banderol, or a product label.

6. The security element according to claim 1, wherein the security element comprises a banknote.

7. The security element according to claim 1, wherein the security element comprises a product label.

8. The security element according to claim 1, wherein the at least three metal atoms in the complex are sequentially arranged and embedded within a triple helix formed by at least three of the benzimidazole molecules.

9. The security element according to claim 1, wherein the helical metallic complex has formula (1):

$$[M_1M_2M_3(L1)_3] \quad (1)$$

wherein:
$M_1$, $M_2$ and $M_3$ are as defined above,
L1 represents each benzimidazole molecule, so as to form a complex with the metal atoms, $M_1$, $M_2$, and $M_3$ surrounded by the three L1, and the metallic complex forming a triad donor ($M_1$)/acceptor ($M_2$)/donor ($M_3$), wherein the efficiency of the intermolecular energy transfer between the pair of donors ($M_1$) and ($M_3$) to the acceptor ($M_2$) is from 30% to 70% and L1 ligand-field strength of the donors ($M_1$) and ($M_3$) is at least 19000 $cm^{-1}$.

10. The security element according to claim 1, wherein the metal atoms $M_1$ and $M_3$ are $Cr^{III}$.

11. The security element according to claim 1, wherein the metal atom $M_2$ is $Er^{III}$.

12. The security element according to claim 10, wherein the metal atom $M_2$ is $Er^{III}$.

13. The security element according to claim 9, wherein the L1 represents formula (2)

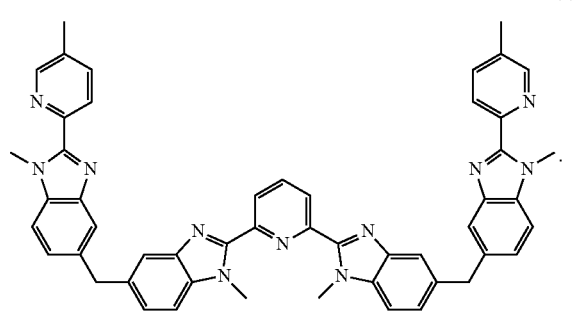

(2)

14. The security element according to claim 9, wherein three molecules of L1 form triple helical structure around each $M_1$, $M_2$ and $M_3$.

15. The security element according to claim 1, wherein the helical metallic complex is soluble in solution and/or gelified solution.

16. The security element according to claim 2, wherein the at least three metal atoms in the complex are sequentially arranged and embedded within a triple helix formed by at least three of the benzimidazole molecules.

17. The security element according to claim 2, wherein the helical metallic complex has formula (1):

$$[M_1M_2M_3(L1)_3] \qquad (1)$$

wherein:
- $M_1$, $M_2$ and $M_3$ are as defined above,
- L1 represents each benzimidazole molecule, so as to form a complex with the metal atoms, $M_1$, $M_2$, and $M_3$ surrounded by the three L1, and the metallic complex forming a triad donor ($M_1$)/acceptor ($M_2$)/donor ($M_3$), wherein the efficiency of the intermolecular energy transfer between the pair of donors ($M_1$) and ($M_3$) to the acceptor ($M_2$) is from 30% to 70% and L1 ligand-field strength of the donors ($M_1$) and ($M_3$) is at least 19000 cm$^{-1}$.

18. The security element according to claim 4, wherein the at least three metal atoms in the complex are sequentially arranged and embedded within a triple helix formed by at least three of the benzimidazole molecules.

19. The security element according to claim 4, wherein the helical metallic complex has formula (1):

$$[M_1M_2M_3(L1)_3] \qquad (1)$$

wherein:
- $M_1$, $M_2$ and $M_3$ are as defined above,
- L1 represents each benzimidazole molecule, so as to form a complex with the metal atoms, $M_1$, $M_2$, and $M_3$ surrounded by the three L1, and the metallic complex forming a triad donor ($M_1$)/acceptor ($M_2$)/donor ($M_3$), wherein the efficiency of the intermolecular energy transfer between the pair of donors ($M_1$) and ($M_3$) to the acceptor ($M_2$) is from 30% to 70% and L1 ligand-field strength of the donors ($M_1$) and ($M_3$) is at least 19000 cm$^{-1}$.

* * * * *